United States Patent
Kircher et al.

(10) Patent No.: US 7,620,479 B2
(45) Date of Patent: *Nov. 17, 2009

(54) METHOD AND APPARATUS FOR CONTROLLING THE STRATEGY OF COMPOUNDING PHARMACEUTICAL ADMIXTURES

(75) Inventors: Joseph J. Kircher, Gurnee, IL (US); Ronald W. Czarny, Cary, IL (US); Robert E. Lewis, Lindenhurst, IL (US); Diane M. Nitzki-George, Deerfield, IL (US); Joe A. Miller, Lake Zurich, IL (US)

(73) Assignee: Baxter International Inc., Deerfield, IL (US)

( * ) Notice: Subject to any disclaimer, the term of this patent is extended or adjusted under 35 U.S.C. 154(b) by 778 days.

This patent is subject to a terminal disclaimer.

(21) Appl. No.: 11/131,088

(22) Filed: May 16, 2005

(65) Prior Publication Data

US 2005/0209737 A1    Sep. 22, 2005

Related U.S. Application Data

(63) Continuation of application No. 09/729,498, filed on Dec. 4, 2000, now Pat. No. 6,975,924.

(60) Provisional application No. 60/168,695, filed on Dec. 3, 1999.

(51) Int. Cl.
*G05B 19/00* (2006.01)
*G05B 21/00* (2006.01)
*B01L 3/02* (2006.01)
*B65B 1/04* (2006.01)
*B65B 3/04* (2006.01)

(52) U.S. Cl. .......... 700/266; 700/265; 422/100; 422/105; 422/108; 436/180; 436/174; 73/61.43; 73/61.44; 141/100; 141/104; 141/105

(58) Field of Classification Search .......... 439/174, 439/180, 43; 700/266; 422/100, 105, 108; 141/100, 104, 10; 73/61.43, 61.44

See application file for complete search history.

(56) References Cited

U.S. PATENT DOCUMENTS 4,513,796 A    4/1985    Miller et al.

(Continued)

FOREIGN PATENT DOCUMENTS

EP    0 320 503    6/1989

(Continued)

OTHER PUBLICATIONS

EP 06 07 5077 Search Rprt, Mar. 7, 2006, Kircher et al.

(Continued)

*Primary Examiner*—Brian R. Gordon
(74) *Attorney, Agent, or Firm*—K&L Gates, LLP

(57) ABSTRACT

A method and apparatus for controlling the compounding of pharmaceutical parenteral admixtures is disclosed. The apparatus preferably comprises a computer that contains a memory for storing instructions for operating the apparatus and for controlling compounders that prepare a prescription admixture, with the memory including data relating to a plurality of the pharmaceutical components that may be transferred to prepare the prescription admixture, and data concerning the operating characteristics of the compounders that the apparatus is adapted to control. The apparatus determines the order of admixing by general rules of admixing and by categorized compatibility groups of components, so that the number of rinses that must be done are minimized.

8 Claims, 11 Drawing Sheets

U.S. PATENT DOCUMENTS

Figure 1:
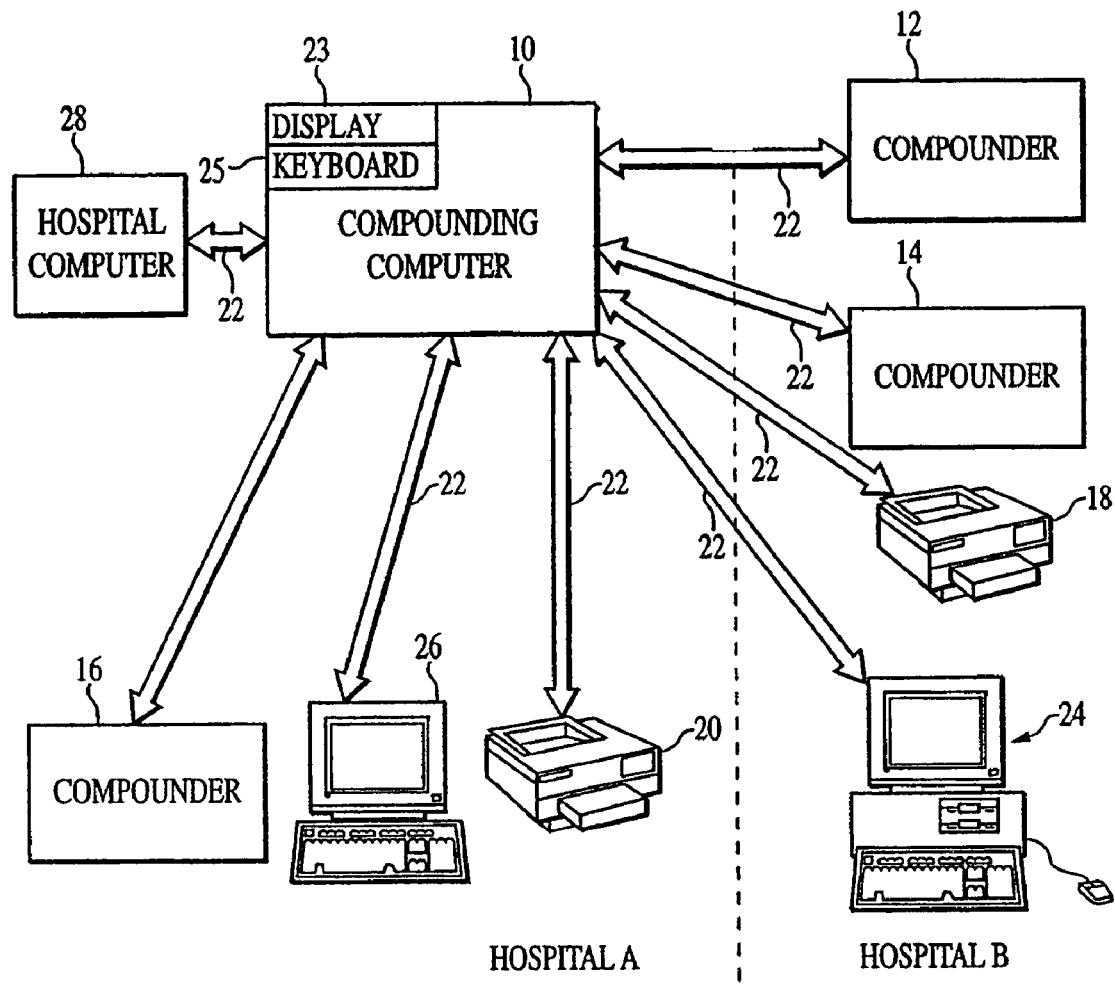

| | | | |
|---|---|---|---|
| 4,648,430 A | | 3/1987 | Di Gianfilippo et al. |
| 4,653,010 A | | 3/1987 | Figler et al. |
| 4,712,590 A | | 12/1987 | Gianfilippo |
| 4,753,775 A | * | 6/1988 | Ebersole et al. ............... 422/81 |
| 4,889,692 A | * | 12/1989 | Holtzman ................... 422/102 |
| 5,040,699 A | | 8/1991 | Gangemi |
| 5,085,256 A | | 2/1992 | Kircher et al. |
| 5,208,762 A | | 5/1993 | Charhut et al. |
| 5,228,485 A | | 7/1993 | Lewis et al. |
| 5,366,896 A | | 11/1994 | Margrey et al. |
| 5,368,898 A | * | 11/1994 | Akedo .......................... 436/48 |
| 5,452,213 A | * | 9/1995 | Ito et al. ..................... 700/117 |
| 5,612,622 A | | 3/1997 | Goldman et al. |
| 5,853,244 A | * | 12/1998 | Hoff et al. ................... 366/141 |
| 5,927,349 A | | 7/1999 | Di Gianfilippo et al. |
| 5,938,938 A | * | 8/1999 | Bosetto et al. .............. 210/739 |
| 5,961,925 A | * | 10/1999 | Ruediger et al. .............. 422/99 |
| 6,149,882 A | * | 11/2000 | Guan et al. .................. 422/211 |
| 6,199,603 B1 | | 3/2001 | DiGianfilippo et al. |
| 6,277,334 B1 | * | 8/2001 | Ecker et al. ................. 422/131 |
| 6,489,168 B1 | * | 12/2002 | Wang et al. ................... 436/37 |
| 6,649,403 B1 | * | 11/2003 | McDevitt et al. ......... 435/288.5 |
| 6,713,298 B2 | * | 3/2004 | McDevitt et al. ......... 435/287.8 |
| 6,975,924 B2 | * | 12/2005 | Kircher et al. ............. 700/266 |
| 2002/0028159 A1 | * | 3/2002 | Lebl et al. ..................... 422/99 |
| 2002/0045265 A1 | * | 4/2002 | Bergh et al. ................... 436/37 |
| 2002/0168292 A1 | | 11/2002 | Whisenhunt et al. |
| 2002/1016829 | * | 11/2002 | Whizenfluet et al. .......... 422/67 |
| 2003/0027345 A1 | * | 2/2003 | Friswell et al. ............... 436/49 |
| 2003/0064422 A1 | * | 4/2003 | McDevitt et al. ........... 435/7.32 |
| 2003/0162226 A1 | * | 8/2003 | Cima et al. .................. 435/7.1 |
| 2005/0118637 A9 | * | 6/2005 | Levinson et al. ............. 435/7.1 |
| 2005/0136548 A1 | * | 6/2005 | McDevitt et al. ............ 436/180 |

FOREIGN PATENT DOCUMENTS

| | | |
|---|---|---|
| EP | 0 320 503 A | 6/1989 |
| EP | 0 721 103 | 7/1996 |
| EP | 0721103 | 7/1996 |

OTHER PUBLICATIONS

"Multitask Operating System for Automix® Compounders Version 2.30, Operator's Manual," Baxter Healthcare Corporation, Deerfield, IL, May 1999.

"MM23™ Compounder Operating Program, Version 4.2," Revision A, Baxa Corporation, Englewood, CO.

"MM23™ Version 4.2x Capabilities and Benefits," Revision A, Baxa Corporation, Englewood, CO.

"Direct Entry™ Compounder Operating Program, Version 1.1," Revisional A, Baxa Corporation, Englewood, CO.

"TPN-PC Plus™ Parenteral Nutrition Program, Version 3.3, "Baxa Corporation, Englewood, CO.

"TPN-PC™ & TPN-PC Plus™ Version 3.3x Capabilities and Benefits," Revision A, Baxa Corporation, Englewood, CO.

"Baxa MicroMacro Compounding Software Version 4.0x Operating Instructions," Revision A, Baxa Corporation, Englewood, CO, Apr. 16, 1993.

"Baxa Micromacro™ Operating Software," Version 4.03, Baxa Corporation, Englewood, CO., Jun. 17, 1993.

"Multitask Operating System for Automix® Compounders Version 2.30, Operator's Manual", Baxter Healthcare Corporation, Deerfield, IL, May 1999.

"MM23™ Compounder Operating Program, Version 4.2," Revision A, Baxa Corporation, Englewood, CO.

"MM23™ Version 4.2x Capabilities and Benefits," Revision A, Baxa Corporation, Englewood, CO.

"Direct Entry™ Compounder Operating Program, Version 1.1," Revision A, Baxa Corporation, Englewood, CO.

"TPN-PC Plus™ Parenteral Nutrition Progream, Version 3.3," Baxa Coporation, Englewood, CO.

"TPN-PC™ & TPN-PC Plus™ Version 3.3x Capabilities and Benefits," Revision A, Baxa Corporation, Englewood, CO.

"Baxa MicroMacro Compounding Software Version 4.0x Operating Instructions", Revision A, Baxa Corporation, Englewood, CO, Apr. 16, 1993.

"Baxa Micromacro™ Operating Software", Version 4.03, Baxa Corporation, Englewood. CO., Jun. 17, 1993.

"Operating Instructions for MicroMacro Compounder", Version 3.O3, Revision F9205, Baxa Corporation, Englewood, CO.

"Quik Instructions for Baxa Micro/Macro™ Compounder Software Version 3.0".

* cited by examiner

METHOD AND APPARATUS FOR CONTROLLING THE STRATEGY OF COMPOUNDING PHARMACEUTICAL ADMIXTURES

This application is a continuation of U.S. application Ser. No. 09/729,498 filed Dec. 4, 2000 now U.S. Pat. No. 6,975,924 which claims the effective filing date of U.S. Provisional Application No. 60/168,695, filed Dec. 3, 1999.

The present invention generally relates to a method and apparatus for preparing and accounting for pharmaceutical admixtures. More particularly, it relates to strategies for preparing prescriptions for parenteral admixtures, for controlling the compounding apparatus, and for properly accounting for the prepared admixture with the strategies being implemented in computer software.

BACKGROUND OF THE INVENTION

Pharmaceutical parenteral admixtures are a combination of sterile drugs that are mixed together under aseptic conditions and are intended for intravenous infusion. These admixtures may be relatively simple or extremely complex, with the complexity increasing with the inclusion of multiple active ingredients. Nutrition admixtures are one example of complex parenteral admixtures that are frequently prepared in a hospital pharmacy for treating patients in the hospital. In general parenteral nutrition admixtures ("PN") refer to most types of nutritional solutions for intravenous feeding. Total patenteral nutrition admixtures ("TPN") generally refer to those PNs that do not contain lipids as a component, and total nutritional admixtures ("TNA") refer to those PN's that contain lipids.

The pharmacy of a hospital, a compounding center or a care facility prepares or compounds a prescription which typically has been determined by a physician singularly or in conjunction with a dietician, pharmacist or other care provider. The pharmacy may be required to compound large numbers of PN on a daily basis. The actual PN compounding is done primarily by electomechanical mixing equipment called compounders which are extremely sophisticated and are adapted to admix many different components in differing proportions as set forth in pharmaceutical prescriptions.

Compounders include high volume compounders which are adapted to prepare PN by transferring those components which are normally found in relatively large volumes in a PN, for example amino acids, sterile water, lipids and dextrose, at a relatively high speed. Such compounders include the AUTOMIX 3+3 compounder manufactured by the Clintec Nutrition Division of Baxter Healthcare Corporation.

Compounders also include low volume compounders such as compounders from the same corporation marketed as a MICROMIX compounder. The MICROMIX compounder is adapted to accurately transfer those components that are normally found in relatively small volumes in a PN.

It is common for pharmacies to produce a prescribed PN by utilizing both a MICROMIX and an AUTOMIX compounder, typically by adding the high volume components to the final container or final bag with the AUTOMIX compounder and then transferring the final bag to the MICROMIX compounder for transferring the smaller volume components. It should be understood that a single compounder may have the capability of transferring both high volume components and low volume components either sequentially or concurrently. Alternatively, the single compounder could have both a high volume module and a low volume module that could transfer fluid to a common manifold, a common transfer tube connected to a final bag or container, or into separate ports in a final bag.

To prepare such PN at an acceptable cost it is important that the PN are compounded as efficiently as possible. Efficiency is generally achieved by seeking to maximize the number of PN's prepared over a given period of time or "throughput". However, the complexity of properly preparing PN tends to slow down such throughput. Areas of complexity may be found in determining the proper PN for a given prescription for a particular patient, accurately preparing the PN and accounting or billing for the PN. However, safety of the patient is paramount and efficient PN preparation must be accomplished with little possibility of errors.

In preparing the proper prescription for a particular patient the pharmacist must perform many tasks including evaluation and determination of the proper components and their respective amounts. Patient specific factors including the type of patient i.e. neonatal, and weight of patient, will be considered. Improving the ability of the pharmacist in making such evaluations and determinations will increase the throughput and reduce the possibility of errors. For record keeping purposes it is desirable and on occasion required for the pharmacist to note in a permanent record why the prescription differs from generally desired amounts of source solutions.

As is well known in pharmacy practice, much of the complexity involved in preparing PN results from compatibility issues relating to the components that are placed in the prescribed PN. Compatibility is defined as the interaction between a drug and all other components with which that drug comes into contact, including but not limited to the diluent, the container and other drugs in the same PN. Compatibility is divided into two subcategories which are physical as well as chemical compatibility. Physical compatibility is defined as an incompatibility that will alter the physical appearance of the drug, typically resulting in a visual change such as precipitation, gas evolution or a change in color. Chemical incompatibilities are not visually observed but must be analytically tested. Chemical incompatibilities occur as a result of changes in the active drug such as oxidation or photodegradation. Factors that can influence compatibility include, but are not limited to the total diluent volume, concentration levels, the order of admixing and the pH.

There are two steps in the evaluation of compatibility and parenteral admixtures. First, compatibility of the entire PN over the period between preparation of the admixture and completion of delivery to the patient should be evaluated prior to compounding. Secondly, the compounding preparation process must be planned in a way to allow for compatibility while the compounding process is proceeding. For example, the compatibility between a source solution being added to the final mixing container or any intermediate mixing container and the solution present in that container should be evaluated. In many instances source solutions which are packaged at concentrations which are incompatible with other solutions must be diluted before they come into contact with each other in such chambers.

As can be appreciated the highest dilution will occur when the greatest amount of diluting fluids are already present in the container into which the solutions are being added. For example, amino acid or dextrose source solutions will form a large portion of a PN and yet are typically compatible with most additives. Thus it would seem to that these solutions would be transferred first to the final container or to any intermediate mixing chambers to dilute added source solutions.

An additional complexity that must be considered is the prevention of the contact between highly concentrated solutions which are incompatible with each other along a common flowpath in the compounder. In a representative instances, although source solutions may flow along separate tubes for much of a transfer flowpath, there may be a section along a transfer flowpath which is common to the two incompatible source solutions. This common flow path may be found along any part of the flow path such as in an intermediate mixing chamber or after the intermediate mixing chamber or after a switching valve.

One method to reduce the possibility of a solution being incompatible with a second solution along a common flow path is to flush the common flow path after each solution has been transferred. Such flushing is accomplished with a solution which is compatible with both the prior solution as well as the solution to be added after the flush. As can be appreciated frequent flushing dilute the incompatible solutions thereby making them compatible but will also decrease throughput.

Also there must be a source of fluid for such a flushing scheme. The source of such flushing solutions may either be a compatible source solution which forms a part of the prescription or the solution present in a downstream chamber such as an admixture in the final mixing container. However, in present pharmacy practices, the prescribed amount of solutions which are used as flushing solutions are typically transferred first to the final container for expediency and dilution purposes and are not available as flushing solutions. In this instance and by default the solution in the final bag must be compatible with the solution which is to be flushed, and the flushing solution will be drawn from the final container. Drawing the flush from the final bag and returning the flush to the final bag decreases throughput. On the other hand holding back an amount of the diluting source solutions for flushing may lead to instances where two incompatible solutions come into contact with each other in the final mixing chamber without being properly diluted to a compatible concentration.

In an effort to increase efficiency, a pharmacist will typically group solution containers in dependence on the operating scheme of the compounder so that ingredients which are compatible with each other (at source solution concentration) are added together sequentially between rinses which are set by the pharmacist. After making a determination regarding the compatibility of the various solutions the pharmacist may group a set of compatible solutions on station 1-4, a second set of compatible of compatible solutions on stations 5-8, etc with rinses set after station 4, station 8, etc. However, a particular admixture may require 5 solutions which are compatible. Because setting rinses requires greater time and effort, the pharmacist may hang the fifth ingredient at a station which has rinses before and after rather than adjust the station arrangement and rinsing scheme. This however is not optimal.

Another consideration for a pharmacist when compounding multiple prescriptions comprising a mixture of TNA and TPN is lipid hazing in which a trace of lipid is present in a final solution which is not to contain lipids. Hazing can be produced by lipids being present in amounts as low as one to 3 parts per million. Such hazing will typically occur when a prescription containing lipids is compounded immediately prior to a prescription which is not to contain lipids. Lipid hazing is not generally believed to create a health hazard, however lipid hazing in a PN which is to be infused may be later mistaken for a PN with unacceptable precipitation arising from an error in formulating a compatible PN solution, and the hazy solution may be mistakenly discarded.

If lipid hazing is an issue the pharmacist may seek to avoid such problems by flushing the compounder after each prescription containing lipids is compounded. However, such flushing will decrease throughput and not be totally effective. To increase throughput, the pharmacist may decrease such flushing by grouping lipid prescriptions; however such groupings have a negative impact on flexibility. If lipid hazing is not an issue, the possibility of lipid hazing should be communicated to persons who are compounding the solution and who are administrating the PN to the patient to prevent the administer from mistakenly believing that the admixture has become unstable.

Other methods of seeking to prevent lipid hazing are to use a completely separate flowpath for the lipids to the final mixing container. However, once lipids are present in a final container flushing or rinsing using solution from the final container will introduce lipids into the flowpath and may cause lipid hazing in a subsequent PN.

Adding to the complexity of compounding the pharmacist must consider is the accuracy limits of the compounders such that prescriptions which have ingredients in volume levels below the accuracy limit of the compounder will likely be added by hand utilizing a syringe. Such manual addition decreases throughput. Also inefficiencies inherent in the administration of the PN to the patient such as residual volumes in administration sets must also be considered. Accounting for the complexities has proven to be time consuming and lead to inefficient activities and practices.

For reimbursement and record keeping purposes, the prepared admixture must be accounted for which is generally accomplished by reporting either manually or electronically transferring information into a facility's accounting system. The steps the pharmacist must perform to insure that an admixture is properly accounted for should be minimized to increase efficiency.

Thus, it is a primary object of the present invention to provide an improved method and apparatus for preparing and accounting for patenteral nutrition solutions. It is a further object of the present invention to provide a method and apparatus for preparing a parenteral admixture to reduce instances of incompatibility, which preferably includes a software implementation of the method that will accommodate many known active ingredients and other components that are set forth in various prescription admixtures. More particularly, it is a related object to provide strategies for preparing prescriptions for parenteral admixtures, for controlling the compounding apparatus, and for properly accounting for the prepared admixture with the strategies being implemented in computer software.

It is another primary object of the present invention to provide such an improved method and apparatus for preparing a parenteral admixture by increasing the throughput of a compounder, principally by minimizing the number of rinses that have to be performed.

A related object of the present invention lies in the provision for selectively determining the order or reorder of a plurality of admixture solutions or compatibility groups that may reside in a prescription, to more efficiently prepare the prescriptions, such as by maximizing the number of prescriptions which may be prepared over a set time period.

A more detailed object of the present invention is to provide such an improved method and apparatus for controlling a compounder of the type which utilizes an intermediate mixing chamber such as a funnel for admixing components prior to transferring the contents of the chamber to the final mixing chamber such as a final bag.

Another object of the present invention lies in the provision of patient specific data to enhance the ability of the pharmacist to efficiently formulate and safely compound admixtures from prescriptions.

Still another object of the present invention is to provide an improved method and apparatus for allowing the pharmacist to efficiently compensate for the accuracy limits of the compounder and inefficiencies in administering the PN to the patient such as the fluid which is lost in the administration sets.

Yet another object of the present invention is to provide an improved method and apparatus which includes a higher concentration formulation of an ingredient to be substituted for a prescribed formulation but determines whether the diluting fluid may be provided by compatible other ingredients so that the volume of the resultant admixture is minimized.

Another object of the present invention is to provide such an improved method and apparatus which controls the compounding to alert users when recommended limits are not being adhered to and such alerts are not accidentally ignored. A related object is to provide for the input and recording of the rationale in overriding a warning.

Another object of the present invention is to provide a method and apparatus which reduces instances or alerts users to the possibility of lipid hazing and the possibility that such lipid hazing will be accidentally mistaken for an unacceptable precipitate.

Figure 2:
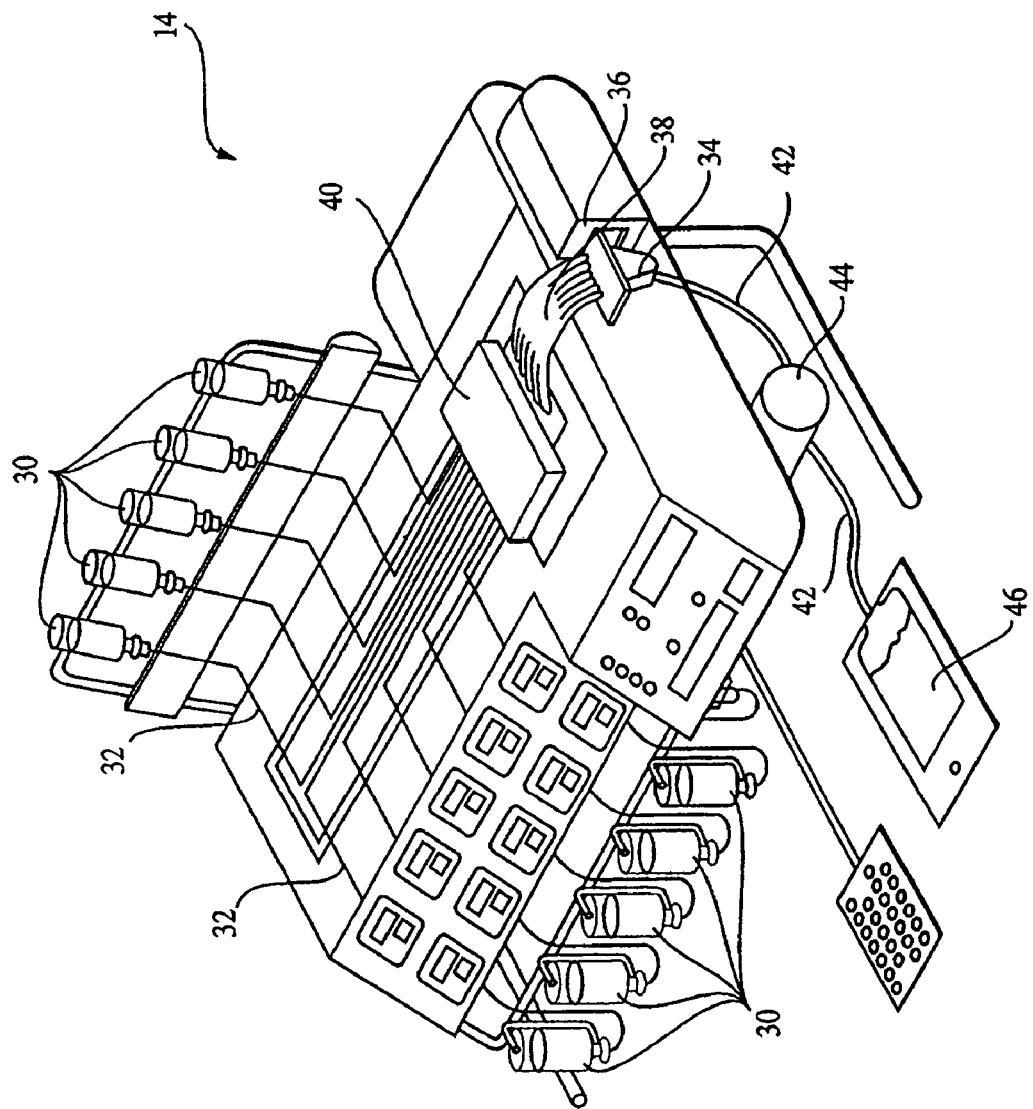
Figure 3:
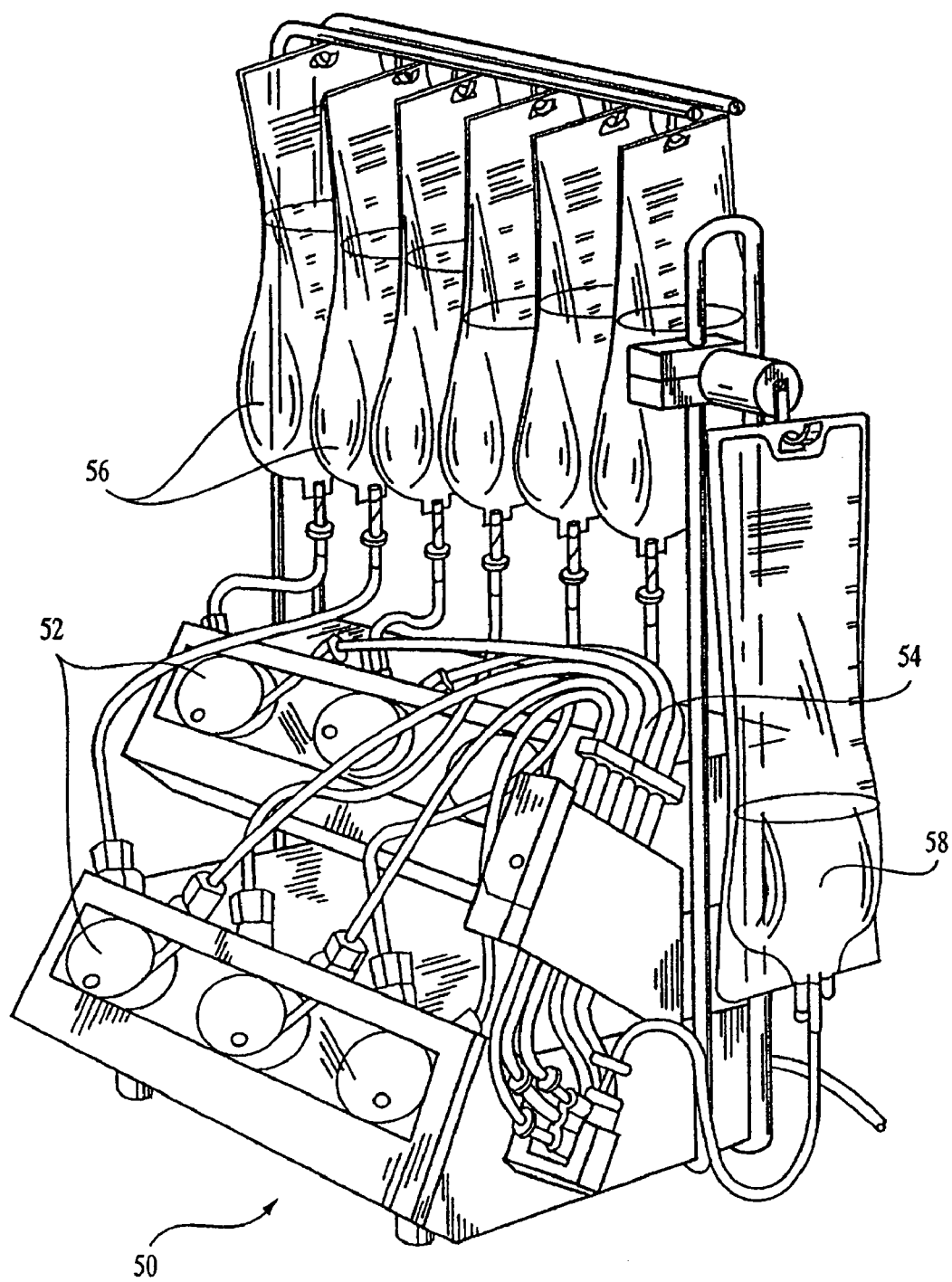

These and other objects will become apparent to those of ordinary skill in the art upon reading the following detailed description, while referring to the attached drawings, in which:

FIG. 1 is a block diagram illustrating the apparatus of the present invention shown in the context of a hospital having a central billing and patient computer which is networked to the apparatus of the present invention and with the apparatus also operatively connected to compounders and printers;

FIG. 2 is a perspective view of a representative compounder that may be controlled by the method and apparatus of the present invention, and particularly showing the compounder having a funnel or intermediate container in which source components are placed either sequentially or concurrently before being transferred to a final bag; and, FIG. 3 is a perspective view of a second representative compounder that may be controlled by the method and apparatus of the presentation.

FIGS. 4a-4h together comprise a flow chart for controlling the compounding of a prescribed admixture in accordance with the present invention.

DETAILED DESCRIPTION

Broadly stated, the present invention is directed to a method and apparatus for controlling the compounding of pharmaceutical admixtures, where the compounding is done by one or more compounders that may be remotely located relative to the controller computer or processing means that is interconnected with the compounders. Referring to FIG. 1, the controller computer or controller 10 has sufficient memory for storing pharmaceutical data in the form of a database as well as operating software for use in controlling compounders and other peripheral equipment. The computer 10 is preferably a multi-user, multi-tasking computer that has a communication interface for interconnecting to compounders 12, 14 and 16 and other peripheral equipment such as printers 18 and 20 by communication links 22 that may be wired or wireless, may be part of a local area network, a wide area network or the Internet or a combination of the above.

The computer 10 may have a display 23 and keyboard 25 as well as other accessories and features common to commercially available computers at this time.

Other peripheral equipment can include a dumb terminal 24 having a keyboard and display or other input device such as a laptop computer 26 or other handheld device that is adapted to enter prescriptions and input instructions for operating the controller computer software. The compounders may be located in different areas of a healthcare facility such as a hospital, or on different floors of a hospital or even at different hospitals. The compounders 12 and 14 as well as the printer 18 and terminal 24 are located in hospital B in FIG. 1, whereas the remainder of the equipment is shown to be located in hospital A. There is preferably a printer located near each compounder or combination of compounders, as shown, for printing labels that are applied to the prescribed admixtures that are compounded. The controller computer 10 is preferably interconnected with a general hospital computer 28 that may be used to prepare and record billing statements among other functions.

The present invention is adapted to control compounders such as compounders 12, 14 and 16. The presence of two machines in hospital B is to indicate that two different types of compounders may be used in combination to prepare prescription admixtures, such as by but one example, the aforementioned AUTOMIX and MICROMIX compounders. Thus, the compounders 12 may be a compounder adapted for transfer of high volume additives and the compounder 14 may be a compounder adapted for low volume additives. Moreover the compounder 16 may be adapted to transfer both high volume and low volume amounts of ingredients.

Referring to FIG. 2, a perspective view of a low-flow module compounder is illustrated and is adapted to transfer small volumes of components such as micro-nutrients and other drugs from individual source containers 30. However, prescription admixtures may be prepared by a single compounder 16 adapted to transfer high volume and low volume additives or multiple compounders attached to a single final bag 46.

In an embodiment when high accuracy is desired such as when low volume additives are being added to a PN the fluids from the containers 30 is transferred through a separate individual fluid conduit 32 to a single intermediate container of funnel 34 that is suspended from a load cell assembly 36. The load cell assembly 36 weighs the total weight of the funnel 34 to develop an output signal, which is indicative of the amount of fluid in the funnel 36 at any given time. The funnel 34 is closed and is connected to a pressure conduit 38 that is connected to a pressure means and occlusion means such as a valve 40 by example. The pressure means is preferably a single peristaltic pump which can selectively create positive and negative pressures in the funnel 34 to control the direction and flow of fluid into and out of the funnel 34. The funnel 34 also is connected to an outlet conduit 42 that extends to a second occlusion means 44 that is interposed between the funnel 34 and the final bag or container 46. By selectively operating the occlusion means 40 and 44, and the pressure means, fluid can be drawn into the funnel and transferred out of it. These same portions of the machine can also control the direction of flow, so that fluid can be transferred into the final bag 46 and can be removed from the final bag for the purpose of rinsing the funnel 34.

A detailed operation of an example of a compounder adapted to transfer low volume components, at least as of approximately April 1990 is described in U.S. Pat. No. 5,228,485 which is assigned to the same assignee as the present invention, and is incorporated by specific reference herein.

The current commercial MICROMIX compounder may embody certain improvements compared to the '485 patent, but is believed to be similar to that described in the patent.

The compounder 12 may also include an assembly that transfers the additives utilizing other methods of operation such as one or more pumping mechanisms and switching mechanism alone or in combination with volumetric delivery methods, possibly including calibration such as the compounding devices supplied commercially by the BAXA Corporation of Englewood, Colo.

Referring to FIG. 3 a further embodiment of a compounder 50 is represented which is particularly suited for transferring large volume additives. The compounder 50 includes a number of individual pumping stations 52 which cooperate with a disposable transfer set 54 to pump fluids from individual source containers 56 to a final container 58. A detailed operation of an example of a compounder adapted to transfer high volume components, at least as of approximately 1999 is described in U.S. Pat. Nos. 4,712,590 and 5,927,349 which is assigned to the same assignee as the present invention, and is incorporated by specific reference herein. The current commercial AUTOMIX compounder may embody certain improvements compared to the '485 and '349 patents, but is believed to be similar to that described in the patent.

Preparing the Prescription

In an example of a process for utilizing the preferred embodiment of the present invention, a physician or other healthcare provider or group of providers determine what is the parenteral nutritional needs of a patient and arrive at a prescription. A pharmacist will then need to convert the prescription into particular amounts or concentration of additives in the PN which is to be administered to the patient. These amounts will vary in dependence on the particular patient. For example the patient may not be able to accept a large amount of fluid parenterally and, the nutritional needs will need to be accomplished within a minimal amount of fluid. One example of a fluid restricted patient is a neonatal patient. To administer the desired amount of an additive in a smaller total volume, the level of concentration of the additive in the final bag 46 may be higher in the PN than if more of a diluent volume could be used. This higher concentration may lead to a greater chance of compatibility problems with other additives in the PN and may exceed acceptable limits for that patient.

Figure 4A:
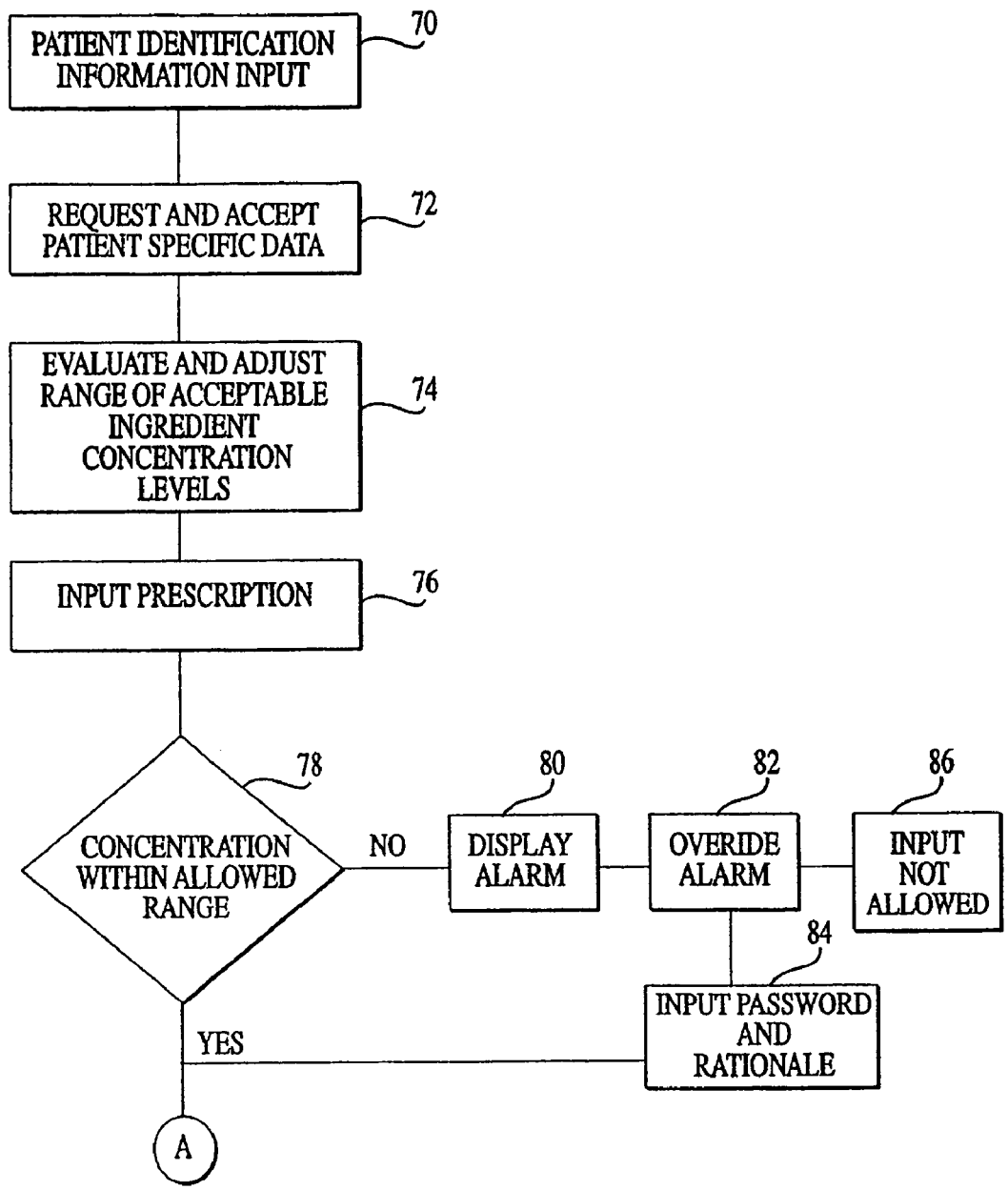

Referring to figure FIG. 4a in the preferred embodiment, the pharmacist enters patient identifying data such as a patient ID code into the controller utilizing the keyboard 25 (block 70). The controller 10 then requests and accepts patient specific data (block 72) from a data storage location such as the computer system 28 of the facility and displays such information on the display 23. One type of patient specific data which is preferably utilized by the controller 10 in the preferred embodiment is the patient type such as premature, neonatal, pediatric or adult, etc. In an alternate embodiment, the provider enters the patient specific data directly into the controller 10 or a storage location therein.

The controller 10 also retains in a storage location preferred ranges for the acceptable concentration levels of the different admixtures in a final bag 46. In an embodiment, the controller 10 may also retain in the data storage location, concentration ranges for the ingredients for the various patient types and set the preferred concentration range with a type dependent range for that particular patient. In a further embodiment ranges corresponding to patient attributes such as various patient ages and weights may be retained in the data storage location and the controller 10 may set the preferred concentration range with attribute specific ranges.

In a further embodiment, the controller may also contain an algorithm for adjusting the concentration range in dependence on predetermined patient specific factors such as the age of the patient.

Thus, in dependence on the patient specific data, the controller 10 may evaluate whether the preferred ranges are appropriate for the patient specific type and may then adjusts the range (block 74).

The health care provider will then enter the prescription (block 76) by, for example, utilizing the keyboard 25. In entering the prescription, the provider will set concentration levels of the ingredient solutions so that upon compounding the PN will correspond to the prescription. The controller 10 allows the prescription to be entered in several different formats. By way of example the controller 10 may accept inputs of the ingredients in percent of the final solution, concentration per unit volume or an amount corresponding to the per unit weight of the patient.

As the provider is entering the prescription the controller 10 checks the entered concentrations against the determined ranges (block 78). If a concentration is entered which is outside the range, an error message is displayed on the display 23. In addition, if the provider enters an ingredient with an inappropriate format an error or alarm message is displayed on the display to alert the health care provider. An example of an inappropriate format is where the concentration is entered in units of measure per the patients weight but the patients weight has not been input as part of the patent specific data.

In an alternate embodiment, after all the concentrations have been entered the controller 10 may then review the various ingredients and highlight with error messages those ingredients which fall outside the range which has been set for that ingredient.

In a further embodiment, templates of various prescriptions corresponding to various patient types may be retained in a storage location. The pharmacist or controller 10 may then call up the template and either accept or adjust the template. In a still further embodiment, a previous prescription of the patient may be retained in a storage location. The pharmacist or controller 10 may then call up the prior prescription and either adjust or accept the prior prescription to be utilized as the present prescription.

When an alarm is displayed. Even though the concentration is outside the range, the concentration may still, in the medical judgement of a provider, be desired. The controller 10 may then in certain predetermined instances allow the provider to override the alarm (block 82). The controller 10 will allow an override upon the occurrence of one or a combination of certain factors. One factor is whether the provider entering the prescription has the clearance to override the particular alarm. Each alarm may require a different level of clearance before the override is accepted. Some alarms may not be overridden.

The identity and clearance level of the provider may be established by a unique password that is requested by the controller 10 and entered at an appropriate time such as at the beginning of the entry of the prescription or at the occurrence of an alarm (block 84). Other methods of establishing the identity of the provider are also contemplated such as keycards, retina scans or the like.

In addition to establishing the clearance of the provider, to verify that the provider is recognizing and appreciating the error message and for record keeping purposes. The controller 10 may require that the rationale for the override be entered into a note screen displayed on the display 23. For certain alarm situations, the controller 10 does not allow any overrides even with a rationale (block 86).

Compatibility Groupings

The preferred embodiment of the present invention evaluates the compatibilies of the ingredients and the solutions into which the ingredient comes into contact during the compounding process and also the solution in the final solution bag 46 after the compounding is complete.

In present practice, the evaluation of the final prepared PN is a process that is routinely performed by pharmacists. The pharmacists compare the components of the final prepared admixture to literature, which has information concerning compatibility. Many times, the literature is not sufficiently specific to the exact type of ingredients in the admixture being prepared, which requires the pharmacist to use professional judgment in deciding whether the resulting admixture will be compatible.

In accordance with the present invention, the overall compatibility evaluation for complex admixtures primarily focuses on the compounding of parenteral nutrition, which broadly includes PN screening and calcium phosphate solubility screening.

The process preferably involves a first screening step of comparing all PN additives to limits set by the controller 10 which may include the steps of setting ranges preferred concentration limits as described above.

A second step involves comparing the final concentration of amino acids, dextrose and lipid based components to the database of tested admixtures. Amino acid comparisons are brand specific. Databases of admixtures have been compiled through the testing of admixtures and also by utilizing published literature. The admixture database preferably comprises concentrations for both stable and unstable admixtures with a notation of the study conditions such as time and temperature. Preferable the database includes admixtures having identified source components such as by example, brand named amino acids.

In the second step, the prescribed admixture is compared to the database of admixtures. Preferably the comparison is first carried out against admixtures having identified source components. If the prescribed admixture falls within some range of a stable admixture the present invention proceeds to the next step without generating a notice to pharmacists. The range may be set by some variance amount, for example by a set percent of the amounts or concentration levels of corresponding base components in a stable admixture.

However, admixtures with matches (or mixed stable and unstable matches) to the unstable formulation contained in the database (to preferably plus or minus a set variation of the amounts of base components) and yet have passed the first screening step may be designated as potentially unstable.

In an embodiment of the present invention, if the prescribed admixture matches an unstable admixture a further step may be performed such as screening whether the study conditions of the matched admixture are equivalent to the present conditions. The present invention provides a warning to pharmacists that the admixture is equivalent to potentially is unstable admixture under the study conditions of that admixture.

In a further embodiment, admixtures that do not match any stable or unstable admixtures contained in the database are re-evaluated. When this is done, the amino acid brand is ignored and the admixture is then compared to the entire database. The results of this comparison are handled following the same steps that have been previously described. Preferably, the pharmacist would be provided a warning about the ignoring of the amino acid brand of the database admixture. If the admixture does not match the database after re-evaluation of the entire database, the present invention will provide a warning notice to the pharmacist that no similar PN has been previously tested.

With regard to calcium phosphate solubility screening, the solubility of calcium salts and phosphate salts in the same solution is dependent on many variables including, but unlimited to concentration, temperature, salt form, order of mixing, pH, amino acids concentration, other additives and time. It has been the practice in the prior art for the pharmacist to compare the final concentration of both the calcium salt and phosphate salt to a solubility curve that is specific to a given amino acids brand and final concentration.

In the present invention, the calcium phosphate solubility screening in a complex compounding process is achieved by the controller 10 comparing the final concentration of both the calcium salt and phosphate salt to a matrix of known compatibility. The matrix may be input into a storage location by the Pharmacist or previously input into the database The present invention uses the matrix to sort compatibility by the amino acids brand and final concentration. For example, a calcium phosphate solubility matrix for a specific amino acids brand may have compatible concentrations of calcium salts and phosphate salts for a 1%, 2% and 4% final amino acid concentration. The present invention determines the limits of solubility that have been exceeded and will generate a warning to the pharmacist if it has.

In a further embodiment, the controller 10 may generate and display on the display 25 a graph of a shape representing the calcium phosphate solubility for that a particular amino acid and may also present a designation of the prescribed admixture relative to the solubility shape to assist the pharmacist in achieving a prescription which is compatible.

However, in addition to the determining whether the prescription present in the final bag is compatible, compatibility during the compounding process must be evaluated. For example, the compatibilities of a solution with a second solution at the time of contact must be evaluated. The second fluid may be found in a common conduit, intermediate mixing chamber or final bag. To overcome this potential problem the pharmacist may adopt gross rules for the compounding process. For example it is common practice that all diluent volumes are added to the final bag first so that all additives which are present in the final bag are diluted as much as possible at the time of the addition of an additional ingredient to the final bag. However, such a practice reduces the ability to rinse from such a diluent during the compounding process.

In accordance with an important aspect of the present invention, the controller computer 10 may utilize the known compatibilities of components to enable concurrent compounding of such compatible components into the final bag or an intermediate mixing chamber. In addition, rinsing may be accomplished with a source solution which is compatible with both the solutions flowing through the rinsed portion before and after the rinsing. Thus, large volume additives may be transferred to the final container or bag or transferred to an intermediate mixing chamber at the same time as small volume additives or used as rinsing fluids. Such compatibility screening and concurrent compounding enables the present invention to maximize the speed in which admixtures are compounded which results in more efficient use of the compounders, as well as the controller computer.

In accordance with an important aspect of the present invention, testing of components for compatibility characteristics is used to build a database that includes a plurality of groups, which represent concentration dependent compatibility on the basis of testing of components. In an example, there are seven groups of components identified in Table 1 set forth below, based upon the current knowledge. It should be understood that many more groups of components may be defined as greater knowledge about compatibility characteristics of various ingredients are acquired, even to the extent of having a group for each individual component, or even separate groups for the same component in different concentrations.

TABLE I

Group Compatibility

| Group | Compatible | Incompatible |
|---|---|---|
| 1 | 1, 2, 3, 6 | 4, 5, 7 |
| 2 | 1, 2, 3, 4, 6, 7 | 5 |
| 3 | 1, 2, 3, 4, 6, | 5, 7 |
| 4 | 2, 3, 4, 6 | 1, 5, 7 |
| 5 | 6 | 1, 2, 3, 4, 5, 7 |
| 6 | 1, 2, 3, 4, 5, 6, 7 | — |
| 7 | 2, 6, 7 | 1, 3, 4, 5 |

The compatibility groups may be known based on test results and are contained in the database of the controller computer so that the compounding process can be carried out with the information in the database. It is preferred that the database be located only in the controller computer, rather than be distributed to various locations so that it can be reliably controlled, managed and modified as additional knowledge and information is gained through history, continued testing, and the addition of other drugs and components to the database.

In a preferred embodiment of the present invention, based upon the database, the controller will logically group the fluids in the source containers 30 (FIG. 2) into the compatibility groups regardless of their physical placement on one of the compounder 12, 14, 16.

In a further embodiment of the present invention, the controller shall calculate for a particular prescription, the number of groups present and the sorting of the groups into sets of compatibility groups between which a rinse is required such that the total number of rinses is minimized.

In a still further embodiment of the present invention the controller utilizes other inputs such as physical restraints of the system to determine the proper compounding sequence to more efficiently utilize source solutions as rinses as opposed to rinses from the final bag. Examples of a physical restraint may include the volume of an intermediate chamber or funnel 34 and the rinse volume for such a chamber.

In an example, the intermediate chamber has a funnel with a volume of 60 ml and a rinse volume requirement of 30 ml. If the prescription calls for 5 ml of Group 1, 20 ml of Group 2; 20 ml of Group 3; 55 ml of Group 4 and 40 ml of Group 6, the controller 10 may adopt a compounding order of Group 1, Group 2, Group 3, Group 6 and Group 4 instead of ascending sequence.

By partially filling the funnel 34 with just Groups 1, Group 2, Group 3, and 10 ml of Group 6, then draining the partially filled funnel before the addition of the remainder of Group 6, at least 30 ml of Group 6 fluid is remaining after the funnel 34 is first filled and this Group 6 fluid can serve as a rinse thereby removing the need to rinse from the final bag.

Other examples of sorting relationships or algorithms may be defined and implemented by the controller to accomplish the desires of the users, such as allocating the volume of a group to other compatible groups to reduce the number of draining of the chamber or funnel 34 may be minimized.

In this regard and reiterating what was stated above, while seven separate groups are contained in Table 1, it is expected that additional groups will be defined, which may be based on more sophisticated knowledge and testing. The precise number of groups will eventually be a function of the sophistication of compatibility knowledge vis-a-vis the all other components that are used, and it is contemplated that a significantly larger number of groups will be defined.

This will lead to the controller computer being able to more accurately control the compounding steps that will result in yet increased efficiency and speed of compounding. Additionally, the database may be considered to be proprietary as its sophistication increases and control of the database at a single location is a significant protection that would not be present if the database were to be distributed to a processor in each compounder, for example.

Compounding Strategies

Figure 4B:
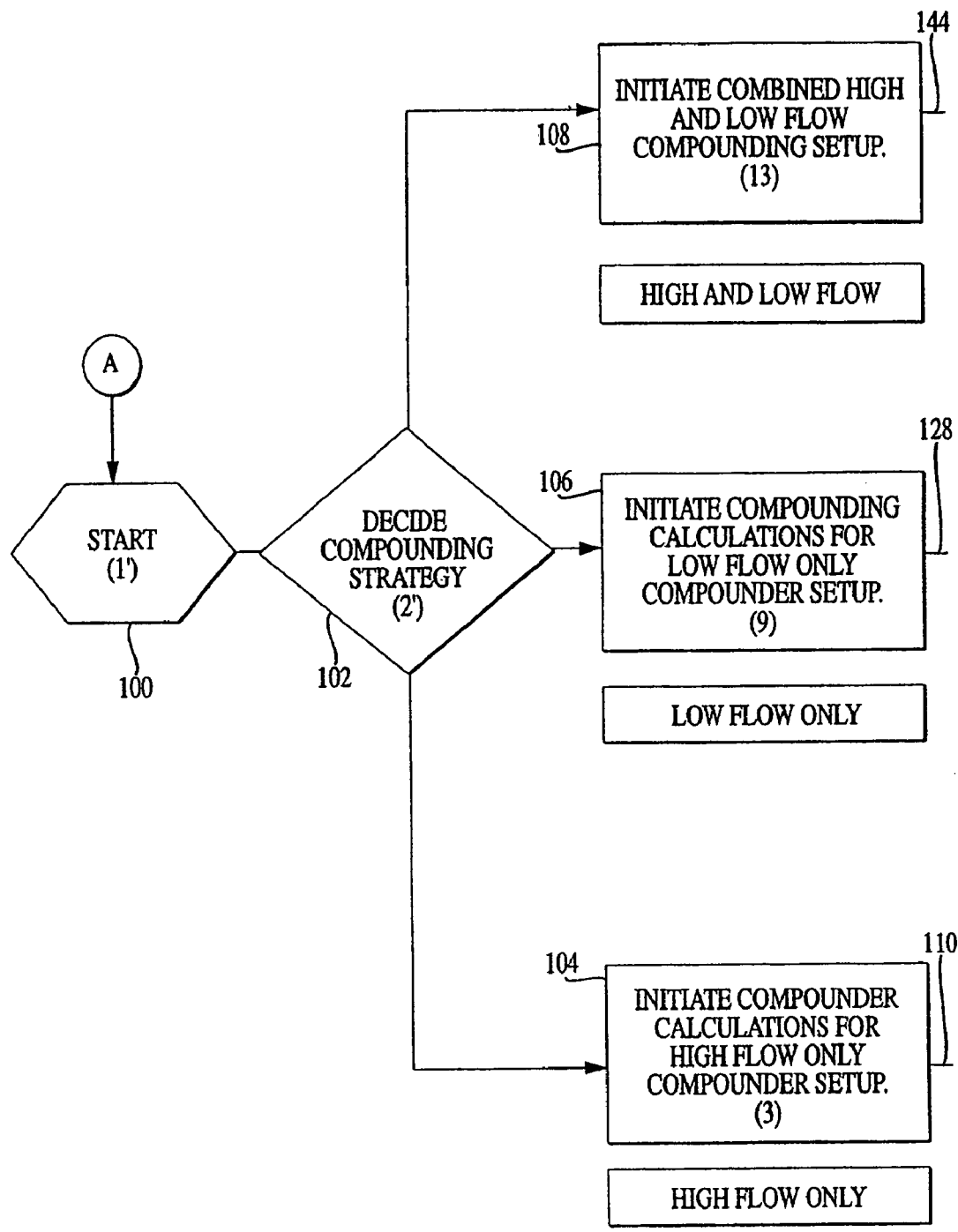

In a further embodiment of the present invention a mixing strategy or method which recognizes the possibility of liquid hazing and utilizing preferably minimizing rinses from the final bag is shown in FIGS. 4b-4h, which illustrates the preferred embodiment of a method of defining the operation of at least one compounder to provide a nutritional formula admixture. The start (block 100) of the method or process is shown in FIG. 4b and occurs after prescriptions have been entered into the controller computer.

In an alternate embodiment of the present inventions the prescription are initially screened by the controller 10 in one or more of the methods described above.

The next step is to decide the compounding strategy (block 102) which is in part dependent upon the kind of compounding equipment that is present.

In this regard, and as previously mentioned, a hospital, other healthcare facility or pharmacy may have only a high-flow module compounder 12 (FIG. 1) which is adapted to transfer high volume fluids at a relatively high flow rate. However, in the event that the facility also has a low-flow module compounder 12, then it can transfer solutions at a low flow rate, which generally enables very small volumes or amounts of a component to be added to a bag. Therefore, in instances where particularly adopted high volume and low volume compounders are utilized, the controller decides compounding strategy (block 2) determines which strategy to employ. The program is adapted to control either a high flow rate (block 104) which would control a high-flow module compounder for example, a low flow rate (block 106) which would control a Low-flow module compounder, for example, or a high and low flow rate (block 108) which would result in both machines being used or for a single compounder 16 suitable for both high volume and low volume transfers, for example.

Referring initially to the high flow only, the controller performs initial compounder calculations for high flow only compounder set up (block 104) which comprises several calculations that the program is will execute for each large volume component that will be part of the final bag. This includes the calculation based on specific gravity to convert volume measure to weight measure, if the transfer is carried out by utilizing the weight of a component that is transferred rather than volume that is transferred. In this regard, a prescription may be written using measurements that are input by grams or milliliters or a percentage of the final solution and the software may be required to convert the measurements to weight, if the compounders transfers in dependence on the sensed weight of the transferred component. For example, the high-flow module 14 and low-flow module compounders 12 compound utilizing the weight or change of weight of an intermediate or final container.

Figure 4C:
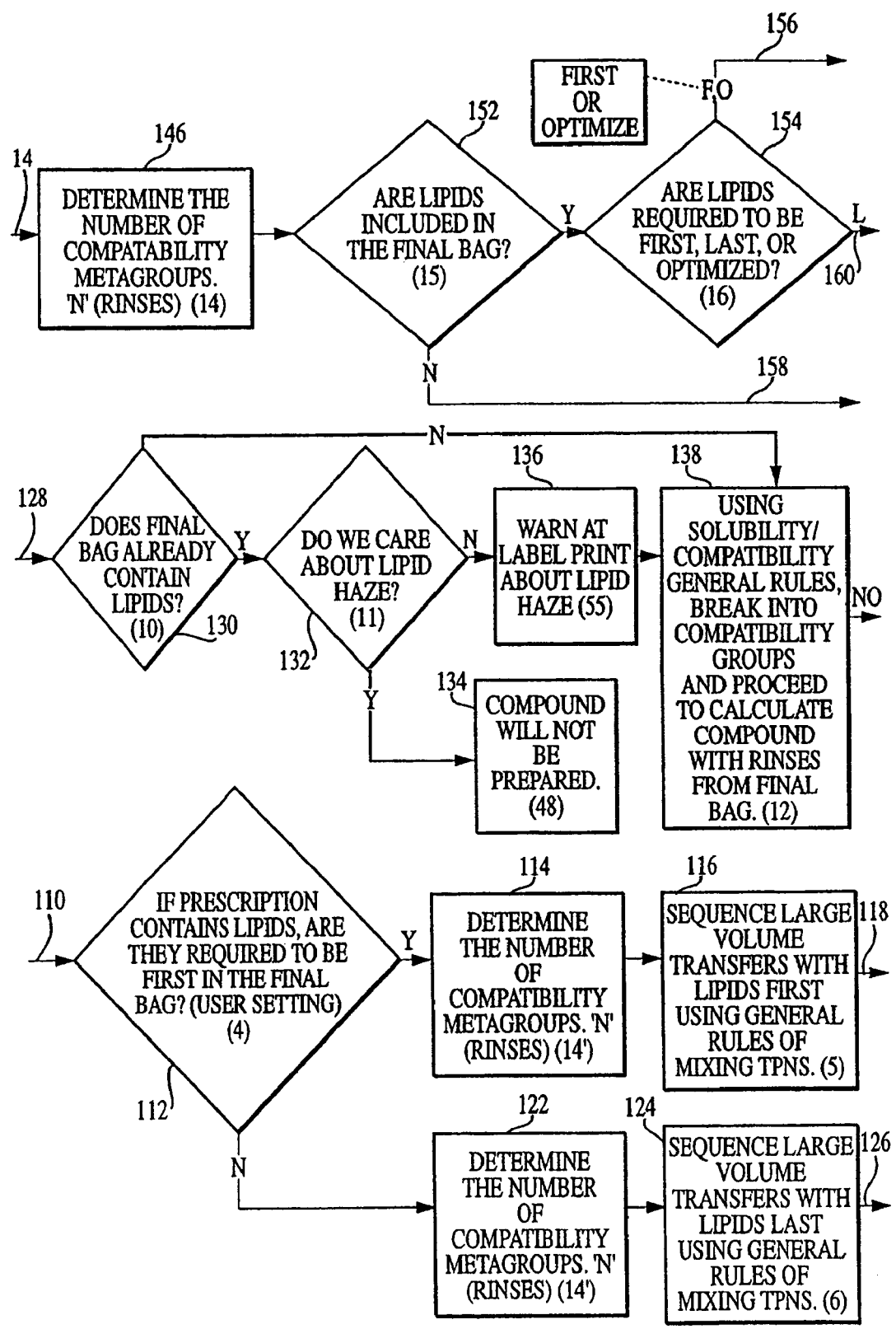

After the calculations are made, line 110 extends to FIG. 4c where a determination is made whether a prescription containing lipids should have the lipids transferred to the final bag first (block 112), which is a user setting. In this regard, users may wish the lipids to be first or last into the final bag, which is strictly an option that the user can specify. Such specification is preferably based on criteria that is set up initially before the compounder is ever run in a facility.

This involves the sorting of all the additives into compatibility groups and this may be done by grouping common compatibility components as shown in the Table 1 above. If lipids are transferred first in the final bag, a determination of the number of compatibility meta-groups is made and the number of rinses N that will be required (block 114) and then the program specifies a sequence of large volume transfers with lipids first. Once the sequence is determined, then line 118 extends to FIG. 4d where the instructions for operating the compounder are transferred to the compounder (block 120).

Alternately the controller 10 can transfer the fluids utilizing other user settings including settings reflecting the general rules of mixing TPN's (blocks 116, 124). With regard to the general rules of mixing total parenteral nutrients, they include the following:

1. Phosphate salts are added before calcium salts.
2. The determination of calcium phosphate solubility should be made based on the volume of solution in the TPN bag at the time calcium is added.
3. Unless lipids are required as the last additive, calcium should always be the last additive to the TPN bag, holding out one rinse, if possible.
4. Compatibility groups are numbered sequentially to coincide with the order of mixing unless specific exceptions are identified.

If the compounder 14 has separate conduits to the final bag for each of the source solutions, the controller 10 sets the order of pumping to insure that the fluid is added to the final bag. The primary determination of the pumping order is the compatibility of the fluid entering the bag with the fluid present in the bag.

Returning to FIG. 4c, if the lipids are not first in the final bag, the number of compatibility groups is also determined, as is the number of rinses required (block 122). The sequence of transfers and rinses with lipids last is determined and executed using one or more of the compounding methods. The final step shown by line 126 that extends to FIG. 4d results in the transfer instructions being sent to the compounder (block 120).

Turning now to the low flow only path which begins with the initiating compounding calculations for low flow only (block 106), this would be used for compounding admixture prescriptions that would be done with a Low-flow module compounder, for example. Even though it is likely that a high flow compounding apparatus would exist in the same area, it is common to choose the low flow compounder if the volume that is going to be added to the final bag is relatively low, such as would occur for a neo-natal prescription or for a very small infusion.

An initial determination is made whether the final bag already contains lipids (block 130). The reason that this determination is made is that there may be a prescription that is compounded in two stages with large volume flow components already being transferred to a bag and the bag is then placed on the Low-flow module for transferring micro-nutrients into it. If lipids are already in the bag, that will make a difference as to how rinses from the final bag are made into a funnel or intermediate mixing chamber which may be present in a low-flow module compounder.

The program determines from the prescription whether lipids are contained in the bag and if so, the entire admixture prescription is checked to determine if lipids are in or will be in the final bag. If they are, then the inquiry is made as to whether the user cares whether there is lipid haze in a following admixture prescription (block 132). This is due to the fact that if any rinse is performed using fluid from the final bag some of the lipids will stay behind in the funnel. These lipids may be transferred to a number of the following bags and in an amount sufficient to produce a visible haze in the solution. If the present bag is made with lipids and the next bag does not have lipids and no rinse of surfaces which will come into contact with the contents of both bags occurs, then there is a possibility that the lipids would haze the next bag, particularly if the prior bag utilizes a rinse from the final bag. In the event that the facility does not desire lipid haze, then the compound will not be prepared at that time but will remain in the queue to be compounded at another time (block 134). If the hospital accepts lipid haze, then a warning is printed by the printer (or by a visual display) indicating that there is a possibility that lipid hazing will exist in the funnel (block 136).

If the final bag does not contain lipids (block 130), or if they do contain lipids but do not care about lipid haze (block 136), then using the solubility and compatibility tables and proceed to calculate the compound keeping in mind that rinses will be from the final bag (block 138). This step is intended to perform calculations that are designed to minimize the number of rinses to maximize efficiency and may utilize one of the methods described above. When this is done, line 140 extends to FIG. 4d and the transfer instructions to the compounder are then sent to the compounder (block 142).

Turning now to the high and low flow branch shown in FIG. 4b, the initial step is to initiate the compounding set up (block 108) which requires the converting calculations be carried out that have been described with respect to the high flow only routine (block 104) and line 144 extends to FIG. 4c, where the number of compatibility groups and rinses is determined (block 146). Basically, it is a determination as to whether there will be a problem with the prescription if it is compounded in the way that it is written.

The determination is made as to whether lipids are included in the final bag (block 152). If lipids are required, the determination is made whether lipids are to be transferred first, last or otherwise optimized (block 154). Whether lipids are required to be first, last or optimized is a user preference that is programmed in the sense that the user defines this once and it is thereafter not prescription dependent. Optimize usually always means that lipids would be placed first. Thus, the criteria for compounding that is established by the user initially will determine the path of steps taken. If they are first or optimized, then line 156 extends to FIG. 4d and FIG. 4c to a step that will be described later. If lipids are not included in the final bag, then line 158 extends to FIGS. 4d and 4e for steps that will also be described later. If lipids are required to be last, then line 160 extends to FIG. 4d and the determination is made whether the prescription is stable without the lipid volume (block 162).

If the prescription is not stable without the lipid volume, the program alerts the user that the prescription cannot be compounded if lipids are last and that a pharmacist check may be required (block 164). The program then determines whether lipids can be transferred into the final bag first (block 166), which if not, results in the compound not being prepared (block 168). If the lipids can be transferred first, then line 170 extends to FIG. 3*d* wherein the number of rinses including the volume of lipids and lipids will be transferred to the final bag first (block 172).

Figure 4D:
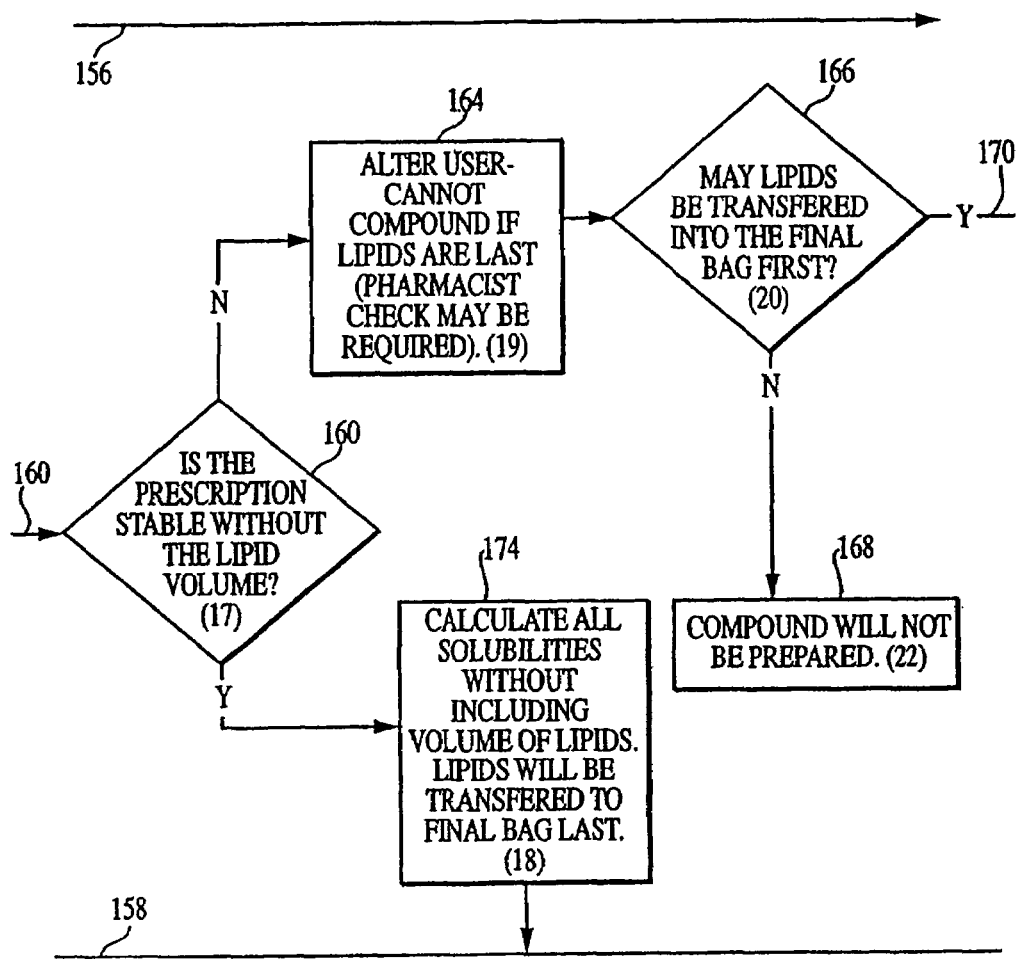
Figure 4D:
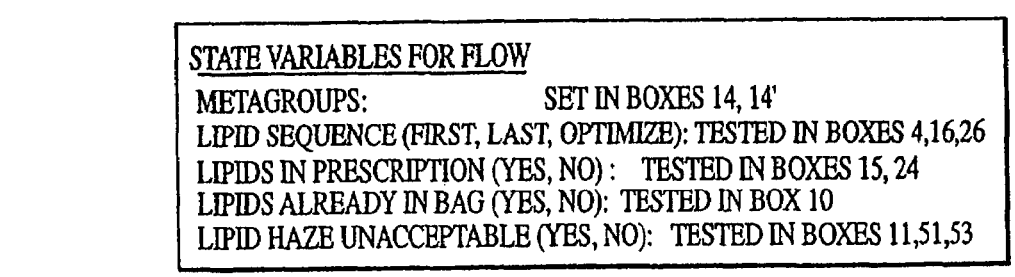
Figure 4D:
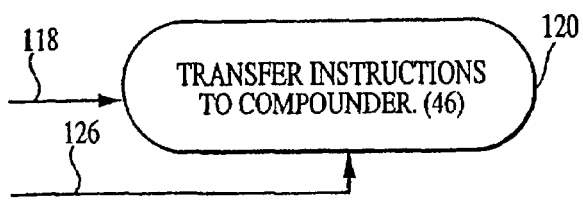
Figure 4E:
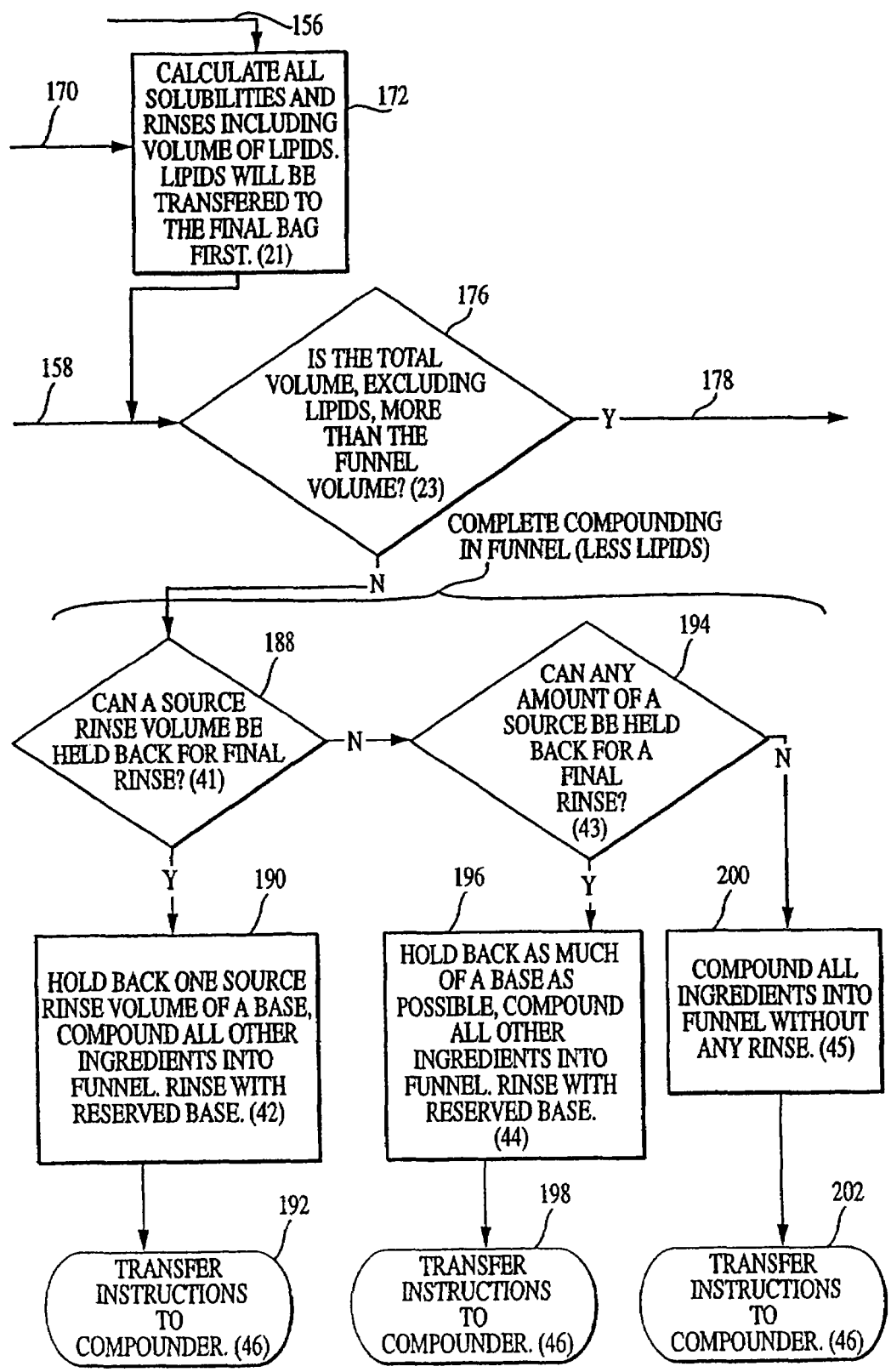
Figure 4F:
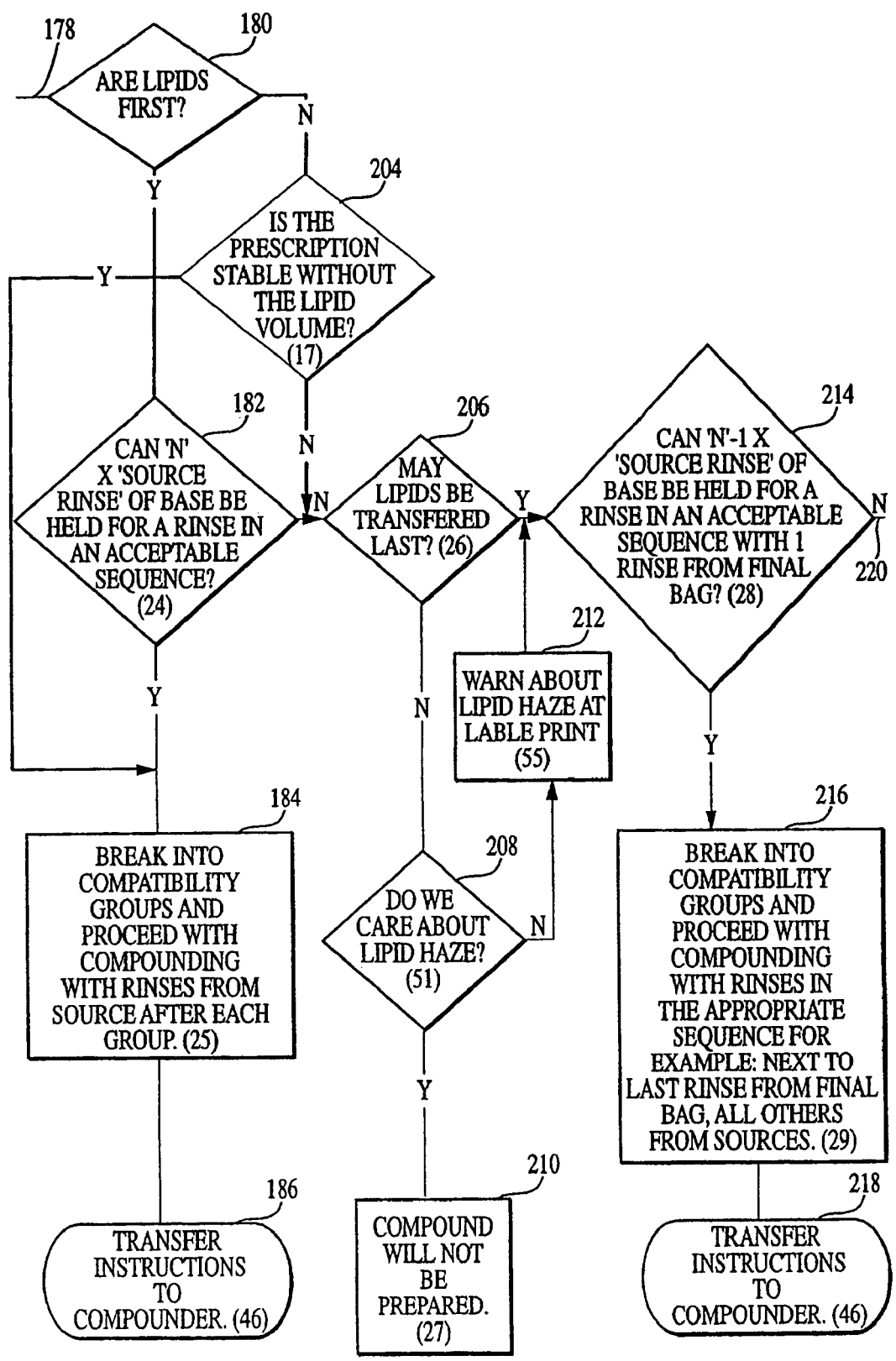

Returning to block 162, if the prescription is stable without including the lipid volume, then the program calculates all solubilities including the volume of lipids and the lipids will be transferred to the final bag last (block 174) (FIG. 4*d*). The calculation of solubilities not including the volume of lipids (block 174) is done to calculate the calcium phosphate solubility based on possibly less volume than what was included in the original screening. Therefore, for example, if there were 50 milliliters of lipids in a 200 milliliter total volume PN, then the phosphate calcium solubility evaluation would be done on 150 milliliters.

After the compatibility groupings and rinses are calculated (blocks 172 and 174), the program then determines whether the total volume excluding lipids is more than the funnel volume (block 176). If yes, line 178 extends to FIG. 4*f* where the program determines whether lipids are first (block 180) which if yes, results in the program determining whether the number of rinses of a source rinse of base may be held for a rinse in an acceptable sequence (block 182). If it can, the program breaks into compatibility groups and proceeds with compounding with required rinses coming from the selected source container (block 184) and the instructions are transferred to the compounder (block 186). As described above the steps that are described in blocks 182 and 184, while identified as separate steps in the flow chart, are really in actuality interrelated. This is because the number of rinses is a function of the compatibility groups and the compatibility groups must be determined in order to identify where rinses should occur as described earlier.

If the total volume excluding lipids is not more than the funnel volume, then the completion of the compounding is done using the low-flow module and can be done in the funnel of the low-flow module compounder. The program determines if a source rinse volume of a component solution can be held back for a final rinse (block 188) which if yes, results in holding back when source rinse volume of a base component and all other ingredients are compounded in the funnel and transferred to the final bag and the funnel is then to be rinsed with the reserve base (block 190) with the rinse transferred to the final bag and transfer instructions are sent to the compounder (block 192).

In order to determine whether a source rinse volume can be held back, it is necessary to screen the fluid present during mixing in the funnel without the diluting effect of the rinse to see if it is permissible to hold anything out, i.e., whether the resulting admixture will be stable. Also, the capacity of the funnel is important with regard to the volume that can be held out for doing a complete rinse. For example, if the funnel capacity is 50 milliliters and only 30 milliliters can be held back, then there will not be a full funnel rinse and the decision as to whether this is adequate or not can be made from the user. It is also contemplated that the method of rinsing will see to have the final rinse originate from a source component such as sterile water, dextrose or amino acids and that intermediate rinses may be made using solution from the final bag with the source rinse of a component volume being held back for the final rinse so that the funnel would be cleaned as much as possible.

If there is not sufficient source rinse volume, the program determines whether any amount of the source rinse volume can be held back for a final rinse (block 194) which if yes, it is done, and all other ingredients are compounded in the funnel and it is rinsed with the reserve base (block 196). The transfer instructions are then sent to the compounder (block 198).

If there is no amount of source that can be held back for the final rinse, all ingredients are then compounded into the funnel without any rinse (block 200) and instructions are sent to the compounder (block 202).

It should be appreciated that from block 152 if the answer is that there are no lipids in the final bag, then the path through the flow chart assuming that the total volume is in excess of the funnel volume results in the determination of whether lipids are first in block 180, which really is not applicable because lipids are not present. In this case, the steps 182 and 184 may be carried out with the source rinse being from source container and/or the final bag. As described above the controller will preferably utilize rinsing and compounding sequence which eliminates the need to rinse from the final bag.

Returning to block 204, if the answer is no, or if the admixture contains lipids, the lipids are to be transferred first and a rinse from a final bag is required (block 182) the program determines if lipids may be transferred last (block 206) which if not, the program inquires whether lipid haze is acceptable (block 208), which if not, results in the compounding not be continued (block 210). If it is acceptable, the program produces a warning about lipid haze (block 212).

If the lipids can be transferred last, then the program determines whether the number of rinses of the source rinse can be held for a rinse and an acceptable sequence can be carried out with one rinse originating from the final bag (block 214). If it can, then the prescription is analyzed for compatibility groups and compounding will proceed with the rinses occurring at the appropriate times with preferably the next to last rinse being done with the final bag with all others from the source components (block 216). In this manner upon rinsing with the contents of the final bag, the ingredients present in the final bag will be diluted as much as possible while allowing for a final source container rinse. The instructions are transferred to the compounder (block 218).

Figure 4G:
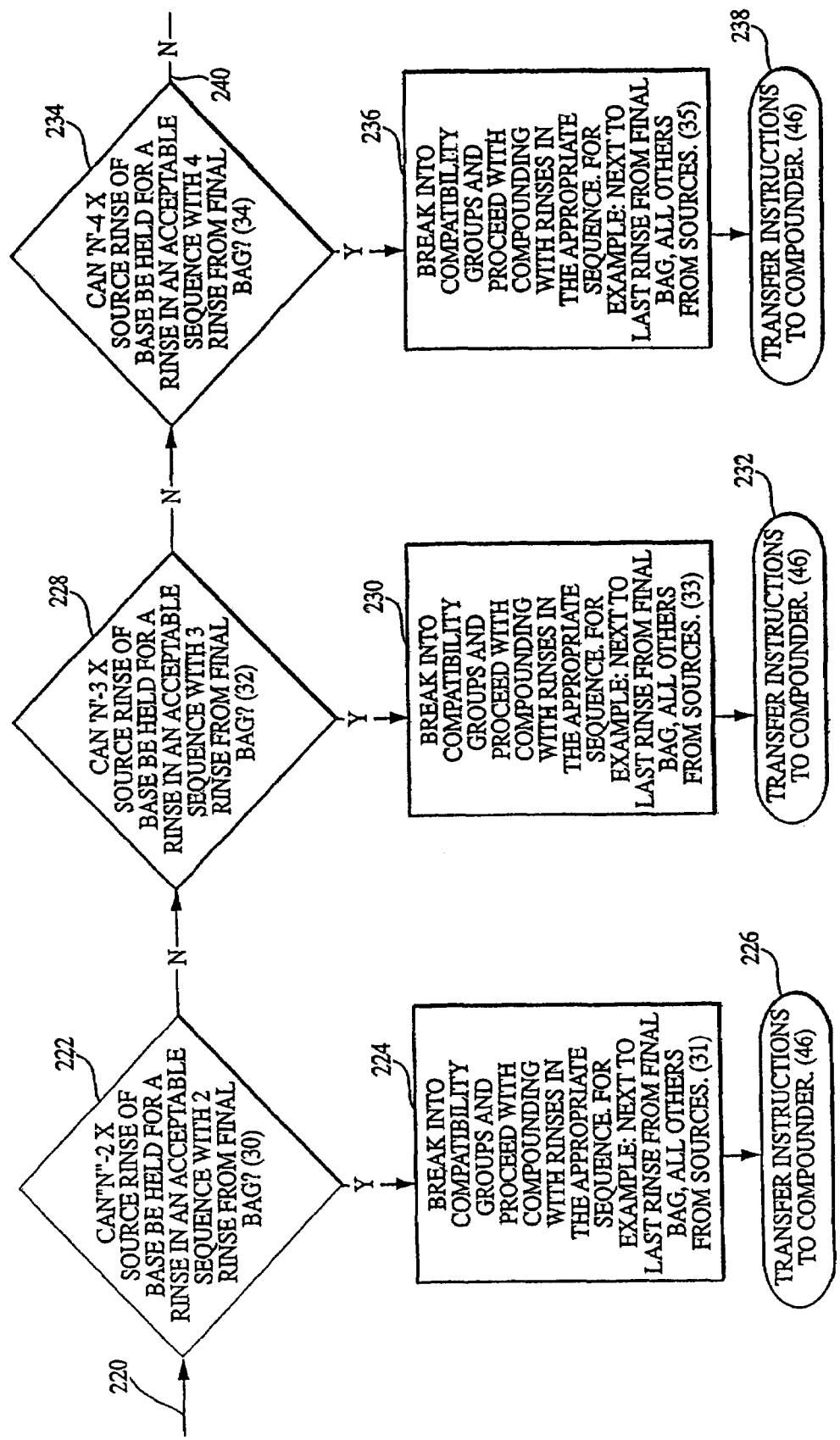
Figure 4H:
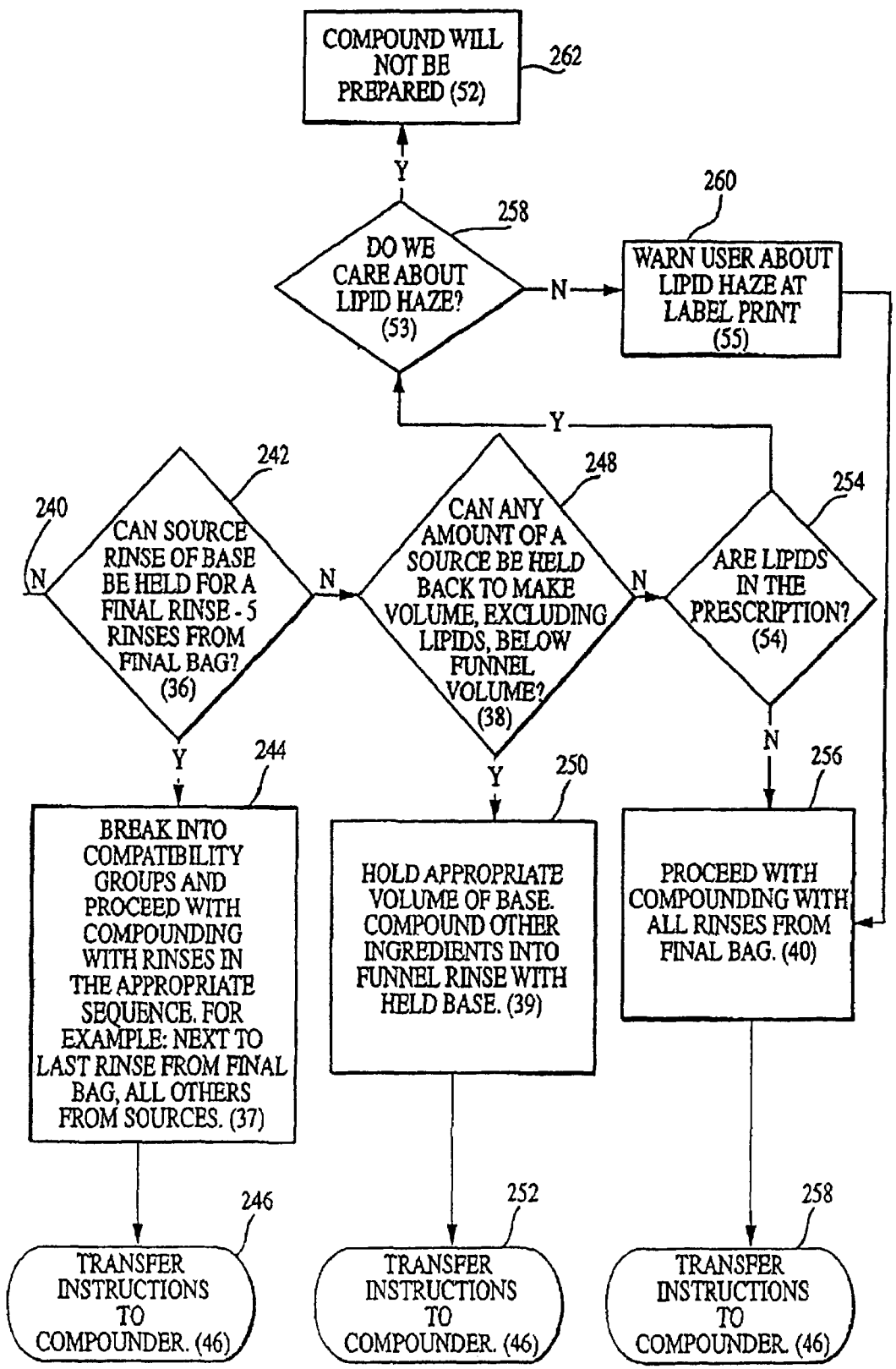

If the answer from block 214 is no, line 220 which extends to FIG. 4*g* results in the program determining if the number of rinses minus 2 (N−2) times the source component rinse can be held for a rinse in an acceptable sequence with two rinses from the final bag being determined (block 222). If yes, then the compatibility group step is again executed (block 224) and instructions to the compounder are issued (block 226). If no, then another determination is made for the number of rinses minus 3 (N−3) (block 228), with compatibility analysis being done if yes (block 230) and transfer instructions are sent to the compounder (block 232). If no, the determination is made regarding N−4 (block 234). If the determination from block 234 is yes, the compatibility analysis is again conducted (block 236) and the instructions are transferred to the compounder (block 238). If the determination is no on line 240, the program then determines if a source rinse can be held for a final rinse (block 242) which if yes, results in the compatibility analysis being carried out once again (block 244) and the compounding instructions being issued (block 246).

If no, the program determines if any amount of source solution can be held back to make the required volume excluding lipids below the funnel volume (block 248). If the answer is yes, then that appropriate volume is held back and the ingredients are compounded in the funnel and the held base component is used to rinse the funnel (block 250) and the transfer instructions are issued to the compounder (block 252). If not, the program determines if lipids are in the prescription (block 254), which if not, results in the program compounding with all rinses originating from the final bag (block 256) and the instructions are issued to the compounder (block 258) but if lipids are present, the program determines whether lipid haze is cared about (block 258). If not, a warning is issued (block 260) and if it is, the compound will not be prepared (block 262). After issuing the warning, the compounding proceeds with all rinses from the final bag (block 256) which results in the transfer instructions being sent to the compounder (block 258).

In sending the instructions to the compounder (blocks 192, 186 etc) the compounder and controller may utilize several methods and adaptations to perform the compounding. For example the controller 10 may send instructions to a controller included as a part of the compounder 12, 14, 16 or the controller may directly operate the compounder or any combination or similar method.

In addition to the compounding strategies that are carried out in the manner described in connection with the flow charts of FIGS. 4a through 4h, there are other functionalities that are carried out by the present invention. In this regard, the controller computer 10 is adapted to examine the composition of each prescription admixture that is present in a queue of such prescription admixtures for which instructions are sent to the compounder that is to prepare the admixture. By examining the components of each prescription admixture in the queue to determine those admixtures which contain lipids, for example, those admixtures which do contain lipids can be group together in order so that lipid hazing is not a concern until the last of the lipid containing admixtures is prepared.

As described in U.S. Pat. No. 4,653,010 prescription admixtures residing in queues may be sorted and grouped around common components. In an embodiment of the invention other desired groupings of admixtures such as by patient type can be determined in a similar fashion. Such reordering of the prescription admixtures in the queue can have the effect of increasing the throughput due to the needs and requirements of a facility.

Another important aspect of the present invention involves the ability of the computer 10 to adjust for a user defined overfill volume by increasing the volume of each of the components that are to be added to the prescription admixture by a predetermined amount to achieve an admixture of equal prescription but a slightly higher volume, and thereby compensate for volume that is required to prime an administrator set or address accuracy concerns when the prescription call for extremely small concentrations of an admixture so that the correct amount of the component in the desired concentration will in fact be delivered to the patient.

Yet another important aspect of the present invention involves the capability of the computer 10 to receive a user switchable option, which when activated, enables a diluted higher concentration ingredient to be substituted for a prescribed lower concentration ingredient. In many instances where the patient is not fluid constrained diluting a higher concentration solution with a compatible rinse solution such as sterile water will produce the prescribed admixture with the minimum amount of potential instability. In a further embodiment of the present invention, particularly when the patient is fluid constrained, the stability of the admixture in eliminating or minimizing the diluting solution by considering other ingredients as diluting fluids is determined by the controller 10 which may employ one of the methods described above to determine stability during and after compounding.

In a further embodiment of the method of the present invention, a compounding strategy for overfilling of the final bag 46 may be performed. As described previously, overfilling may be desired to compensate for the amount of admixture, which may not be administered due to the system of administration. For example some portion of the solution may be retained in a final bag even after administration.

In keeping with an aspect of the present invention, the desired method of setting the overfill may be particularly configured. By way of example the overfill volume may be set in absolute amounts, by a percent or so that the final bag will have a specific desired volume. In preparing such a prescription, the method calculates the new amounts of ingredients required to achieve an admixture substantially equivalent to the prescribed admixture but at a slightly greater volume.

Upon determining the proper ingredient amounts of the ingredients, the controller 10 may check the resulting admixture against various criteria to determine if the resulting admixture may be administered. For example for a fluid restricted patient, an overfill may generate an admixture with an amount of fluid in excess of the allowable amount. An alarm may be generated an error message may be displayed to the user.

In a further embodiment, the controller 10 may adjust or suggest the adjustment of the volume of the admixture to avoid having one or more of the ingredients in an amount less than a predetermined level is such as that which corresponds to the minimum accuracy amount suggested for a compounder 12, 14, 16. By way of example, the amount of a component may be 90% of the minimum suggested amount. The controller may then increase the total volume of the admixture such that the amount of the component reaches the minimum suggested amount and indicate to the user that only of a portion of the resulting admixture is to be administered to the patient.

In should be understood that the arrangement of the steps in the various preferred embodiments of the present invention may be altered. For example the stability of the final admixture may be determined before or after the determination of the proper compounding strategy.

Reporting

The compounder 12, 14, 16 may communicate to the controller 10 during and after the compounding process. For example, should a sensing device as described in U.S. Pat. No. 5,927,349, incorporated by specific reference herein, detect an incorrect source solution flowing through one of the conduits 32 an alarm may be communicated. Similarly, during and after compounding the exact quantities of the ingredients transferred to the final bag 46 may be transmitted to the controller 10.

Upon receiving the amounts of the ingredients transferred during compounding, the controller 10 may present cost data to the pharmacist or communicate such data to the hospital computer system 28. The controller 10 may adjust the cost data to reflect the actual cost of providing the admixture. By way of example, some ingredients may come in containers which can only be accessed once before discarding. Thus if such an ingredient is used in an amount less than that in a container, the controller 10 will indicate the cost of the entire container as opposed to that portion of the ingredient used in the admixture.

From the foregoing, it should be appreciated that an improved method and apparatus for controlling the preparation of parenteral admixtures has been described, which results in faster, more efficient preparation of the same without sacrificing safety in any way. Moreover, several of the features provide added safeguards. The present invention employs an extensive analysis of admixture components and utilizes known characteristics of components in a novel fashion to control compounders so that such prescription admixtures can be reliably and safely prepared without violating known rules of preparation, but also in a manner consistent with certain user defined preferences.

While various embodiments of the present invention have been shown and described, it should be understood that other modifications, substitutions and alternatives are apparent to one of ordinary skill in the art.

What is claimed is:

1. A method of controlling at least one pharmaceutical compounder to prepare a plurality of prescription admixtures, the method utilizing a controller having a memory for storing instructions for controlling the at least one compounder to prepare the plurality of prescription admixtures, the method comprising:

receiving data in the controller via a communication interface, the data being indicative of the plurality of prescription admixtures;

examining the data indicative of the plurality of prescription admixtures in the controller to determine a subset of prescription admixtures that contain lipids;

determining a preparation order for the plurality of prescription admixtures in the controller that groups the subset of prescription admixtures together;

generating instructions in the controller for preparing the plurality of prescription admixtures, the instructions being indicative of the preparation order; and communicating the instructions for preparing the plurality of prescription admixtures from the controller to the at least one pharmaceutical compounder.

2. A method as defined in claim 1, wherein receiving the data indicative of the plurality of prescription admixtures includes receiving the data indicative of the plurality of prescription admixtures via a communication port.

3. A method as defined in claim 1, wherein examining the data indicative of the plurality of prescription admixtures to determine the subset of prescription admixtures that contain lipids includes examining data indicative of components of each prescription admixture in a data queue.

4. A method as defined in claim 1, wherein determining the preparation order for the plurality of prescription admixtures includes determining the preparation order for the plurality of prescription admixtures that minimizes a number of lipid hazing events.

5. A method as defined in claim 1, wherein the preparation order for the plurality of prescription admixtures is associated with a first number of lipid hazing events, and a received order associated with receiving the data indicative of the plurality of prescription admixtures is associated with a second number of lipid hazing events, the first number of lipid hazing events being less than the second number of lipid hazing events.

6. A method as defined in claim 1, wherein determining the preparation order for the plurality of prescription admixtures includes determining the preparation order for the plurality of prescription admixtures that minimizes a number of compounder flushes associated with lipid hazing.

7. A method as defined in claim 1, wherein the preparation order for the plurality of prescription admixtures is associated with a first number of compounder flushes, and a received order associated with receiving the data indicative of the plurality of prescription admixtures is associated with a second number of compounder flushes, the first number of compounder flushes being less than the second number of compounder flushes.

8. A method as defined in claim 1, wherein communication the instructions for preparing the plurality of prescription admixtures to the at least one pharmaceutical compounder includes communicating the instructions for preparing the plurality of prescription admixtures to the at least one pharmaceutical compounder via a communication port.

* * * * *

UNITED STATES PATENT AND TRADEMARK OFFICE
CERTIFICATE OF CORRECTION

| | | |
|---|---|---|
| PATENT NO. | : 7,620,479 B2 | Page 1 of 1 |
| APPLICATION NO. | : 11/131088 | |
| DATED | : November 17, 2009 | |
| INVENTOR(S) | : Kirchner et al. | |

It is certified that error appears in the above-identified patent and that said Letters Patent is hereby corrected as shown below:

On the Title Page:

Item (74) change "K&L Gates, LLP" to --K&L Gates LLP--

In Column 1, line 30, change "patenteral" to --parenteral--

In Column 8, line 47, change "judgement" to --judgment--

In Column 12, line 6, change "vis-a-vis" to --vis-à-vis--

In Column 20, line 30, change "communication" to --communicating--

Signed and Sealed this

Sixth Day of July, 2010

David J. Kappos
*Director of the United States Patent and Trademark Office*